[19] United States Patent
Eckenhoff

[11] Patent Number: 4,963,141
[45] Date of Patent: * Oct. 16, 1990

[54] DISPENSING SYSTEM FOR ADMINISTERING BENEFICIAL AGENT FORMULATION TO RUMINANTS

[75] Inventor: James B. Eckenhoff, Los Altos, Calif.

[73] Assignee: Alza Corporation, Palo Alto, Calif.

[*] Notice: The portion of the term of this patent subsequent to Sep. 12, 2006 has been disclaimed.

[21] Appl. No.: 380,044

[22] Filed: Jul. 17, 1989

Related U.S. Application Data

[63] Continuation of Ser. No. 151,384, Feb. 2, 1988, Pat. No. 4,865,598, which is a continuation of Ser. No. 766,235, Aug. 16, 1985, abandoned.

[51] Int. Cl.[5] .............................................. A61K 9/22
[52] U.S. Cl. .................. 604/892.1; 424/438; 424/473
[58] Field of Search ............... 604/892.1, 890.1, 891.1; 424/472, 473, 438

[56] References Cited

U.S. PATENT DOCUMENTS

| | | | |
|---|---|---|---|
| 2,340,037 | 1/1944 | Zipper | 167/83 |
| 3,732,865 | 5/1973 | Higuchi et al. | 128/260 |
| 3,760,804 | 9/1973 | Higuchi et al. | 128/260 |
| 3,769,805 | 9/1973 | Higuchi | 128/260 |
| 3,845,770 | 11/1974 | Theeuwes et al. | 128/260 |
| 3,929,132 | 12/1975 | Higuchi | 128/260 |
| 3,987,790 | 10/1976 | Eckenhoff et al. | 128/260 |
| 3,995,632 | 12/1976 | Nakano et al. | 128/260 |
| 4,034,756 | 7/1977 | Higuchi et al. | 128/260 |
| 4,088,864 | 5/1978 | Theeuwes et al. | 219/121 |
| 4,178,361 | 12/1979 | Cohen et al. | 424/22 |
| 4,196,187 | 4/1980 | Dannelly et al. | 424/21 |
| 4,235,236 | 11/1980 | Theeuwes | 128/260 |
| 4,285,987 | 8/1981 | Ayer et al. | 427/3 |
| 4,298,003 | 11/1981 | Theeuwes et al. | 128/260 |
| 4,320,759 | 3/1982 | Theeuwes | 128/260 |
| 4,326,522 | 4/1982 | Guerrero et al. | 424/438 |
| 4,327,725 | 5/1982 | Cortese et al. | 128/260 |
| 4,381,780 | 5/1983 | Holloway | 604/892 |
| 4,449,983 | 5/1984 | Cortese et al. | 424/473 |
| 4,595,583 | 6/1986 | Eckenhoff et al. | 424/15 |
| 4,865,598 | 9/1989 | Eckenhoff | 604/892.1 |

FOREIGN PATENT DOCUMENTS

| | | |
|---|---|---|
| 19250 | 3/1972 | Australia . |
| 2729068 | 11/1979 | Fed. Rep. of Germany . |
| 1540258 | 9/1968 | France . |
| 2122086 | 1/1984 | United Kingdom . |
| 2140687 | 12/1984 | United Kingdom . |

Primary Examiner—C. Fred Rosenbaum
Assistant Examiner—C. Maglione
Attorney, Agent, or Firm—Edward L. Mandell; Paul L. Sabatine; Steven F. Stone

[57] ABSTRACT

A dispensing device is disclosed for delivering a beneficial agent. The device comprises (1) a housing defining an internal space, (2) an expandable composition in the space, (3) an aqueous sensitive beneficial agent formulation in the space, and (4) at least one passageway in the housing for delivering the beneficial agent from the dispensing device.

8 Claims, 2 Drawing Sheets

DISPENSING SYSTEM FOR ADMINISTERING BENEFICIAL AGENT FORMULATION TO RUMINANTS

CROSS-REFERENCE TO RELATED APPLICATIONS

This application is a continuation of U.S. patent application Ser. No. 07/151,384 filed Feb. 2, 1988, allowed as U.S. Pat. No. 4,865,598 on Sept. 12, 1989; which application Ser. No. 07/151,384 is a cont. of application Ser. No. 06/766,235 filed Aug. 16, 1985, abandoned; which applns. are incorporated herein by reference and benefit is claimed of their filing dates. These applns. are assigned of record to ALZA Corporation of Palo Alto, CA.

FIELD OF THE INVENTION

This invention pertains to a novel and useful dispensing system for administering a beneficial agent formulation to an animal. Specifically, the invention concerns a dispensing system comprising (1) an outer wall, (2) an internal compartment, (3) a beneficial agent formulation that is insoluble to very soluble in aqueous and biological fluids in the compartment, (4) a hydrogel in the compartment that absorbs fluid and expands for displacing beneficial agent formulation from the dispensing system, and (5) a density member in the compartment for increasing the density of the dispensing system for keeping the dispensing system in the animal over time.

BACKGROUND OF THE INVENTION

It is well known the ruminant animals, including cattle, sheep, giraffe, deer, goat bison, and more particularly cattle and sheep, comprise an important group of animals that are able to digest large quantities of feeds. These feeds are swallowed with little chewing and they are ingested into the largest of the four stomachs of the animal, called the rumen. The rumen, however, is not a true stomach inasmuch as it does not have any digestive glands. The rumen is in the nature of a storage compartment, a mixing organ, and a reservoir containing a large concentration of bacteria. The bacteria in the rumen break up the components of feed into simpler substances which are more readily digested by the animal. The feed next is regurgitated by the animal, masticated into finer particles, and then reswallowed by the animal. After the feed particles are reduced to a certain critical size, they pass out of the rumen for further digestion in the other stomachs of the animal.

The veterinary industry has long sought a dispensing system manufactured in the form of a dispensing device that can reside in the rumen over an extended period of time, for releasing a beneficial therapeutic, nutrient or additive agent formulation into the rumen, at a controlled rate over a corresponding extended period of time. The industry seeks a dispensing system because beef cattle, growing calves and sheep graze over a wide pasture and it is highly inconvenient to administer a single dose unit or multiple dose units of a beneficial agent formulation to an animal. Furthermore, ranchers, farmers and feed lot operators lack the time necessary for administering a single or a multiple dose unit to the animal. The need for a dispensing system is sought especially where continual administration is needed for the health and the management of the animal.

There is, therefore, in view of the above presentation, a pressing need for a veterinary dispensing system that can function as a controlled release intra-ruminal device, and after a single admittance remains in the rumen and efficiently dispenses a beneficial agent formulation into the rumen over a prolonged period of time. There is also a need for an intra-ruminal device that is easily swallowed by the ruminant and remains in the rumen for a long period of time for prolonged release of a beneficial agent formulation in the rumen without being regurgitated by the ruminant.

OBJECTS OF THE INVENTION

Accordingly, it is a primary object of this invention to provide both a novel and useful veterinary dispensing system for use in ruminants that fulfills the pressing needs known to the prior art.

Another object of the invention is to provide a veterinary dispensing system manufactured as an intra-ruminal device that delivers a beneficial agent formulation at a controlled rate over a prolonged period of time.

Another object of the invention is to provide a veterinary dispensing system that remains in the rumeno-reticular sac for an extended period of time and which dispensing system releases a beneficial agent formulation at a rate controlled by the dispensing system.

Another object of the invention is to provide a dispensing device wherein the release rate therefrom of a beneficial agent formulation is rate controlled by the dispensing device and is essentially time independent during the course of beneficial use thereof.

Another object of the invention is to provide a veterinary intra-ruminal dispensing device that is useful for delivering a beneficial agent formulation that is difficult to deliver and can be delivered by the dispensing device at meaningful rates over time.

Another object of the invention is to provide a veterinary dispensing device comprising a compartment containing a beneficial agent formulation that can be from insoluble to very soluble in an aqueous or biological fluid, an expandable driving means consisting of a hydrogel that operates to expand and diminish the space occupied by the beneficial agent formulation, and a density means having a specific gravity greater than the specific gravity of the fluid present in the rumen for keeping the dispensing device in the rumen over time.

Another object of the invention is to provide a dispensing device comprising a compartment containing a beneficial agent formulation and a composition comprising an expandable means and a density means having a specific gravity greater than 1, which combination means expands and displaces the beneficial agent formulation from the dispensing device and keeps the dispensing device in the environment of use over time.

Another object of the invention is to provide a dispensing device that can perform a complete pharmaceutical, nutritional, or anti-infectious regimen for a particular time period, the use of which requires intervention only for initiation and possibly the termination of the regimen.

Other objects, features, aspects and advantages of the invention will be more apparent to those versed in the dispensing art from the following detailed specification taken in conjunction with the drawing figures and the accompanying claims.

BRIEF DESCRIPTION OF THE DRAWING FIGURES

In the drawing figures, which are not drawn to scale, but are set forth to illustrate various embodiments of the invention, the drawing figures are as follows:

FIG. 1 is a view of a dispensing system designed and manufactured as a dispensing device for administering a beneficial agent formulation to an animal over a prolonged period of time;

FIG. 2 is an opened view of the dispensing system of FIG. 1, through 2—2 the vertical axis of the delivery system, for illustrating the structure of the dispensing system comprising an outside wall, a compartment, a beneficial agent formulation, an expandable member and a density member for administering a beneficial agent formulation to an animal, and more particularly a warm-blooded ruminant animal;

In the drawings and in the specifications, like parts in related figures are identified by like numbers. The terms appearing earlier in the specification and in the description of the drawing figures, as well as embodiments thereof, are further detailed elsewhere in the disclosure.

DETAILED DESCRIPTION OF THE DRAWING FIGURES

Figure 1:
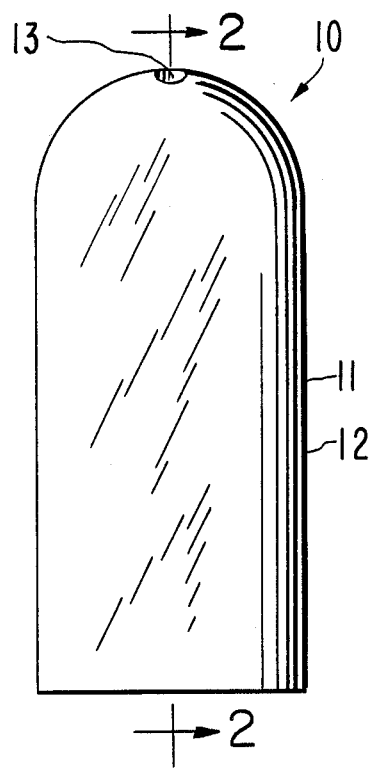

Turning now to the drawing figures in detail, which are examples of a new and useful dispensing system for dispensing a beneficial agent formulation, and which examples are not to be construed as limiting, one example of a dispensing system is seen in FIG. 1, identified by the number 10. In FIG. 1, dispensing system 10 is manufactured as a dispensing device shaped and sized for oral admittance into the gastrointestinal tract of an animal. In FIG. 1, dispensing device 10 comprises a body 11 formed of a wall means 12 that surrounds and forms an internal compartment, not seen in FIG. 1. Dispensing device 10 comprises a passageway 13 indicated by a partial opening in wall 12 for delivering a beneficial agent formulation from dispensing device 10.

Figure 2:
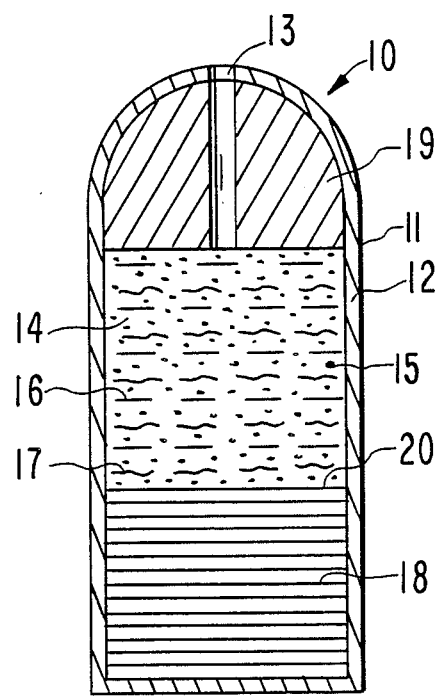

FIG. 2 is an opened view of dispensing device 10. Dispensing device 10 of FIG. 2 comprises body 11, wall 12 and passageway 13. Wall 12 surrounds an internal compartment 14 or lumen. Wall 12 is formed in a presently preferred embodiment in at least a part of a wall forming composition that is permeable to the passage of an external fluid. Wall 12 can be completely formed of a semipermeable composition that is permeable to the passage of fluid and substantially impermeable to the passage of a beneficial agent and other ingredients in compartment 14. Compartment 14 contains a beneficial agent formulation 15, identified by dots, that can be from insoluble to very soluble in fluid present in the environment of use. When beneficial agent formulation 15 is soluble in the fluid, it exhibits an osmotic pressure gradient across a semipermeable composition comprising wall 12 against an external fluid that is imbibed into compartment 14. When beneficial agent formulation 15 exhibits limited solubility, or is substantially insoluble in an external fluid, it exhibits a limited, or it may not exhibit any osmotic pressure gradient activity across a semipermeable composition comprising wall 12 against the external fluid. When agent 15 has a limited solubility, or it is substantially insoluble in external fluid, it can be mixed with an osmagent 16, indicated by dashes, that is soluble in the external fluid and exhibits an osmotic pressure gradient across a semipermeable composition comprising wall 12 against the fluid.

Beneficial agent formulation 15, in another embodiment, can be present in compartment 14 along with carrier means 17, identified by wavy lines. Beneficial agent formulation 14 can be homogeneously or heterogeneously dispersed with carrier means 17. Carrier means 17 is non-heat absorbing, is a hydrophilic polymeric composition, and it is soluble, or it is a lightly cross-linked polymer. In a preferred embodiment carrier means 17 is an osmopolymer possessing osmotic properties including the ability to imbibe and absorb fluid, and exhibit an osmotic pressure gradient across semipermeable wall 12 against an external fluid. Carrier means 17 forms a dispensable formulation with fluid imbibed into compartment 14 and with beneficial agent 15 that is dispensed through passageway 13 from dispensing device 10.

Compartment 14 further contains an expandable member 18 that is, in one embodiment presently preferred, in layered contacting arrangement at the interfaced contacting surface 20 formed by driving member 18 and beneficial agent formulation 15, the latter in combination with osmagent 14 or osmopolymer 17. Expandable member 18 has a shape that corresponds to the internal shape of compartment 14. Compartment 14 also contains a dense member 19 or densifier that is in contact with passageway 13 and beneficial agent formulation 15. A passageway 20 extends through dense member 19 for delivering beneficial agent formulation from compartment 14 to the exterior of dispensing device 10. Passageway 20 is in alignment with passageway 13 in outer semipermeable wall 12 for complete communication between compartment 14 and the exterior of dispensing system 10.

In operation, dispensing device 10 delivers the beneficial agent formulation to a fluidic, biological environment of use by dispensing device 10 performing a combination of thermodynamic and kinetic integrally coordinated activities. That is, first beneficial agent, or beneficial agent osmagent formulation, or beneficial agent osmopolymer formulation, in either embodiment, imbibes fluid through a semipermeable wall into the compartment to form a dispensable solution containing beneficial agent or a dispensable soft, paste-like osmopolymer containing beneficial agent. As the dispensable composition is formed, concomitantly external fluid is imbibed through the external semipermeable wall by expandable hydrophilic layer 18 in a tendency towards osmotic equilibrium, to continuously expand and swell layer 18. Layer 18 expands, in a presently preferred embodiment, with an intact immiscible boundarY at interface 20 defined by the beneficial agent formulation and the expandable layer. The expansion and continuous swelling of layer 18 increases the volume of layer 18, and simultaneously layer 18 expands in compartment 14, thereby urging beneficial agent formulation through passageway 20 and 13. The combined operation of fluid imbibition by beneficial agent formulation, and the displacement of the beneficial agent formulation by the expandable layer, occurs at a controlled rate over a prolonged period of time, usually about one day to six months or longer. Dense member 19 keeps dispensing device 10 in the rumen during this period of time.

Figure 3:
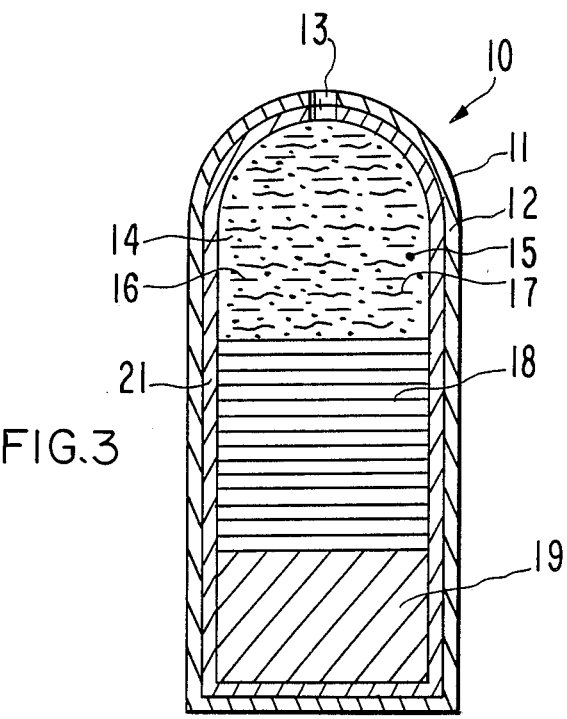
FIG. 3 is an opened view of FIG. 1 through 2—2, with FIG. 3 illustrating another embodiment of the dispensing system comprising an inside wall forming member and a different arrangement of the components present in the compartment.

FIG. 3 is an opened view of another dispensing device provided by the invention. Dispensing device 10 of FIG. 3 comprises exterior wall 12, internal compartment 14, beneficial agent 15, osmagent 16, or osmopolymer 17, expandable hydrogel 18, in a presently preferred embodiment comprises a different material than the material forming osmopolymer 17, and weight 19. Dispensing device 10 also comprises an internal wall 21 that can be formed as a single capsule member, or formed as a dual section member. Internal wall 21 is formed of a different wall forming composition than the composition forming wall 12. Dense member 19 in dispensing device 10 of FIG. 3 is positioned distant from passageway 13. In this latter embodiment, expandable member 18 exerts a direct force on the beneficial agent formulation 15, thereby urging it through passageway 13.

Figure 4:
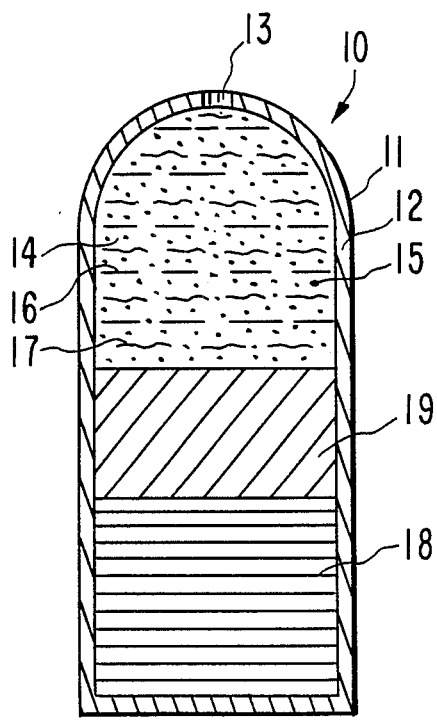
FIG. 4 is an opened view of FIG. 1, with FIG. 4 illustrating yet another embodiment provided by the invention wherein all the elements of the dispensing system are in concert for the controlled delivery of a beneficial agent formulation over an extended period of time from one day to six months.

FIG. 4 depicts another manufacture provided by the invention. FIG. 4 is an opened view of the dispensing system of FIG. 1, and it depicts a different internal management with density member 19 positioned between the beneficial agent formulation and the expandable driving member. In this manufacture, density member 19 is solid and its position in compartment 14 negates the presence of a passageway in said dense member 19. The face of the density element, in an optional embodiment, proximal to the orifice may geometrically conform to the curvature of the dispenser at the passageway to discharge completely the beneficial agent.

Figure 5:
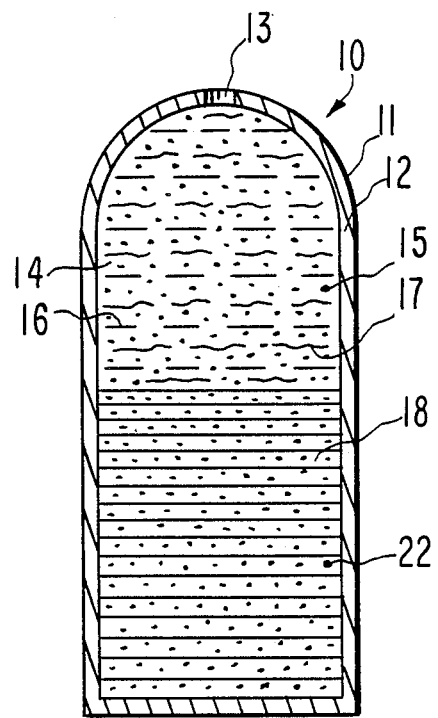
FIG. 5 is an opened view of the dispensing system of FIG. 1, illustrating an embodiment wherein the expandable means and the density means are compounded into a unit composition of matter.

FIG. 5 depicts another manufacture provided by the invention. FIG. 5 is similar to the dispensing devices described, supra, except that in FIG. 5, dispensing device 10 comprises expandable member 18, contains a density producing member 22, identified by dots, dispersed therein. The presence of density member 22 in expandable member 18 is a component of dispensing device 10 for keeping dispensing device 10 in the rumen of an animal during the beneficial agent dispensing period. Dispensing device 10 operates in the manner described above.

Figure 6:
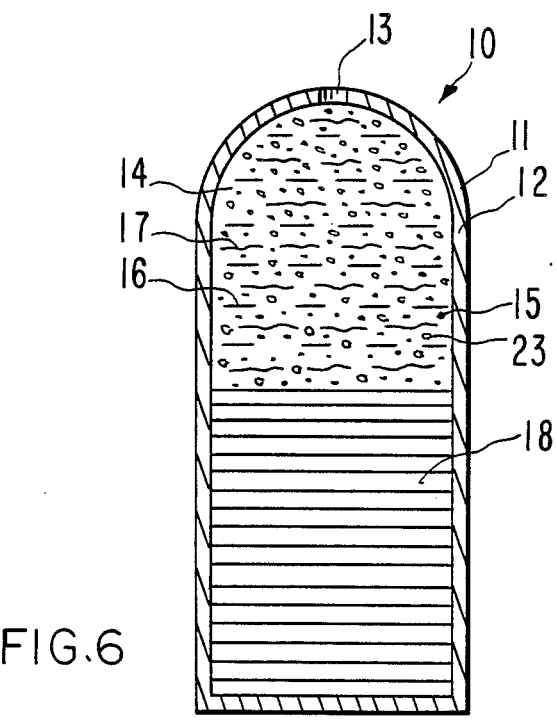
FIG. 6 is an opened view of the dispensing system of FIG. 1 illustrating another embodiment of the invention wherein the compartment comprises a combination composition of a beneficial agent formulation and a density member possessing a specific gravity greater than one.

FIG. 6 illustrates another manufacture provided by the invention. Dispensing device 10 of FIG. 6 is similar to the dispensing devices described for examples 1 through 5, except that in FIG. 6 dispensing device 10, a density producing member 23, identified by circles, is homogeneously or heterogeneously dispersed throughout the beneficial agent formulation. In this embodiment, as beneficial agent formulation is delivered through passageway 13 from dispensing device 10 it transports therewith density member 23. Furthermore, as the beneficial agent formulation leaves dispensing device 10 and transports density member 23 therewith, dispensing device 10 becomes lighter enabling it to pass from the environment of use at the end of the dispensing period.

Dispensing device 10 can be manufactured in a variety of sizes and shapes for administering device 10 to warm-blooded animals, including ruminant animals. One presently preferred shape is a cylinder-like or capsule-like shape. For example, for use with sheep, delivery system 10 can embrace a capsule-like shape and have a diameter of about 0.5 inches to 2.5 inches (1.3 cm to 6.6 cm). For use with cattle, system 10 has a diameter of about 1 inch to 3.5 inches (2.5 cm to 7.8 cm), and a length of 3.0 inches to 5.0 inches (7.2 cm to 12.2 cm). While FIGS. 1 through 6 illustrate various delivery systems 10 that can be made according to the invention, it is to be understood these systems are not to be construed as limiting the invention, as the dispenser can take other shapes, sizes and forms for delivering beneficial agents to the biological environment of use. The delivery system Can be used in veterinary clinics, farms, zoos, laboratories, on the range, in feed lots, and other environments of use. The dispensing device can be used for dispensing a beneficial agent formulation to a fluid environment of use, wherein the fluid environment is an aqueous environment which aqueous fluid includes biological aqueous type fluids.

DETAILED DESCRIPTION OF THE INVENTION

In accordance with the practice of this invention, it has now been found representative materials for forming a wall 12 include, in a presently preferred embodiment, semipermeable homopolymers, and semipermeable copolymers, exemplified by cellulose monoesters, cellulose diesters, cellulose triesters, cellulose ethers, and cellulose ester-ethers, mixtures thereof, and the like. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxy, halogen, carboalkyl, alkylcarbamate, alkyl carbonate, alkylsulfonate, alkylsufamate, and like semipermeable polymer forming groups. The semipermeable materials typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di- and tri-alkenylates, mono-, di and tri-aroylates, and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S. of 2 to 3 and an acetyl content of 34 to 44.8%, and the like. More specific cellulosic polymers include cellulose propionate having a D.S. of 1.8 and a propionyl content of 38.5%; cellulose acetate propionate having an actyl content of 1.5 to 7% and an acetyl content of 39 to 42%; cellulose acetate propionate having a acetyl content of 2.5 to 3%, an average propionyl content of 39.2 to 45% and a hydroxyl content of 2.8 to 5.4%; cellulose acetate butyrate having a D.S. of 1.8, and acetyl content of 13 to 15%, and a butyryl content of 34 to 29%; cellulose acetate butyrate having an acetyl content of 2 to 29.5%, a butyryl content of 7 to 52%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate; cellulose propionate morpholinobutyrate; cellulose acetate butyrate; cellulose acetate phthalate, and the like; mixed cellulose esters such as cellulose acetate valerate, cellulose acetate succinate, cellulose propionate succinate, cellulose acetate octanoate, cellulose valerate palmitate, cellulose acetate heptonate, and the like. Semipermeable polymer are known in U.S. Pat. No. 4,077,407, and they can be made by procedures described in *Encyclopedia of Polymer Science and Technology,* Vol. 3, pp 325 to 354, 1964, published by Interscience Publishers, Inc., NY.

Additional polymers include cellulose acetaldehyde dimethyl cellulose acetate; cellulose acetate ethylcarbamate; cellulose acetate methylcarbamate; cellulose dimethylaminoacetate; a cellulose composition comprising cellulose acetate and cellulose hydroxypropyl methylcellulose; a cellulose composition comprising cellulose acetate and cellulose acetate butyrate; a cellulose composition comprising cellulose acetate butyrate and hydroxypropyl methylcellulose; semipermeable polyamides; semipermeable polyurethanes; semipermeable polyurethanes; semipermeable polysulfane; semipermeable sulfonated polystyrenes, cross-linked, selectively semipermeable polymers formed by the coprecipitation of a polyanion and a polycation as disclosed in U.S. Pat. Nos. 3,173,876; 3,276,586; 3,541,005; 3,541,006 and 3,546,142; selectively semipermeable silicon rubbers; semipermeable polymer as disclosed by Loeb and Sourirajan in U.S. Pat. No. 3,133,132; semipermeable polystyrene derivatives; semipermeable (polysodiumstyrenesulfonate); semipermeable poly(vinylbenzyltrimethyl) ammonium chloride; semipermeable polymer exhibiting a fluid permeability of $10^{-1}$ to $10^{-7}$ (cc.mil/cm$^2$ hr.atm) expressed as per atmosphere of hydrostatic or osmotic pressure difference across a semipermeable wall. The polymers are known to the art in U.S. Pat. Nos. 3,845,770; 3,916,899 and 4,160,020, and in *Handbook of Common Polymers* by J. R. Scott and W. J. Roff, 1971, published by CRC Press, Cleveland. OH.

In the manufacture wherein device 10 comprises an internal wall formed from a capsule member, the capsule member generally is tubular shaped and it has a mouth at one end, and the end distant therefrom is closed in a hemispherical or dome-shaped end. The capsule member serves as a hollow body having a wall that surrounds and defines an interior compartment provided with an opening for establishing communication with the exterior of the capsule and for filling the capsule. In one embodiment, a capsule is made by dipping a mandrel, such as a stainless steel mandrel, into a bath containing a solution of a capsule wall forming material to coat the mandrel and trimmed to yield a capsule with an internal lumen. The materials used for forming the capsule are then commercially available materials including gelatin, gelatin having a viscosity of 15 to 30 millipoises and a bloom strength up to 150 grams; gelatin having a bloom value of 160 to 250; a composition comprising gelatin, glycerine water and titanium dioxide; a composition comprising gelatin, erythrosin, iron oxide and titanium dioxide; a composition comprising gelatin, glycerine, sorbitol, potassium sorbate and titanium dioxide; a composition comprising gelatin, acacia, glycerin and water; water soluble polymers that permit the transport of water therethrough and can be made into capsules, and the like.

The wall also can comprise a flux regulating agent. The flux regulating agent is a compound added to a wall forming composition that assists in regulating the fluid permeability of flux through the wall. The flux regulating agent can be a flux enhancing agent or a flux decreasing agent. The agent can be preselected to increase or decrease the liquid flux. Agents that produce a marked increase in permeability to fluid such as water, are often essentially hydrophilic, while those that produce a marked decrease to fluids such as water, are essentially hydrophobic. The amount of regulator in the wall when incorporated therein generally is from about 0.02% to 20% by weight or more. The flux regulator agents in one embodiment that increase flux include polyhydric alcohols, polyalkylene glycols, polyalkylenediols, polyesters of alkylene glycols and the like. Typical flux enhancers include polyethylene glycol 300, 400, 600, 1500, 4000, 6000 and the like; low molecular weight glycols such as polypropylene glycol, polybutylene glycol and polyamylene glycol; the polyalkylenediols such as poly(1,3-propanediol), poly(1,4-butanediol), poly(1,6-hexanediol) and the like; ailphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; ester such as ethylene glycol diproprionate, ethylene glycol butyrate, butylene glycol dipropionate glycerol acetate esters, and the like. Representative flux decreasing agents include phthalates substituted with an alkyl, an alkoxy or with both an alkyl and alkoxy group such as diethyl phthalate, dimethoxyethyl phthalate, dimethyl phthalate, and [di(2-ethylhexyl)phthalate]; aryl phthalate such as triphenyl phthalate, and butyl benzyl phthalate; insoluble salts such as calcium sulphate, barium sulphate, calcium phosphate, and the like; insoluble oxides such a stitanium oxide; polymers in powder, granule and like form such as polystyrene, polymethylmethacrylate, polycarbonate, and polysulfone; esters such as citric acid esters esterified with long chain alkyl groups; inert and substantially water impermeable fillers; resins compatible with cellulose based wall forming materials, and the like.

Other materials that can be used to impart flexibility and elongation properties to wall 12, for making the wall less-to-nonbrittle, and for increasing tear strength include plasticizers, presently exemplified by phthalate plasticizers such as dibenzyl phthalate, dihexyl phthalate, butyl octyl phthalate, straight chain phthalates of six to eleven carbons, diisononyl phthalate, diisodecyl phthalate, and the like. The plasticizers include nonphthalates such as triacetin, dioctyl azelate, epoxidized tallate, triisoctyl trimellitate, triisononyl trimellitate, sucrose acetate isobutyrate, epoxidized soybean oil and the like. The amount of plasticizer in a wall when incorporated therein is about 0.01% to 20% by weight, or higher.

Expandable means 18 preferably has a shape that corresponds to the internal shape of compartment 14 and it is made from a hydrogel composition. The hydrogel composition is noncross-linked or optionally cross-linked and it possesses properties, such as the ability to absorb or imbibe an exterior fluid through the wall, and, when it is an osmopolymer, it exhibits an osmotic pressure gradient across a semipermeable wall against a fluid outside delivery system 10. The materials used for forming the swellable, expandable inner layer 18 are polymeric materials neat, and polymeric materials blended with osmotic agents that interact with water or a biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, and osmopolymers, can be noncross-linked or lightly cross-linked. The cross-links can be covalent or ionic bonds with the polymer possessing the ability to swell in the presence of fluid, and when cross-linked it will not dissolve in the presence of aqueous fluid. The polymer used for the purpose of expandable means 18 generally will exhibit a viscosity of 5,000 to 10,000,000 centipoise at 25° C. The polymers can be of plant, animal or synthetic origin. Polymeric materials useful for the present purpose include poly(hydroxyalkyl methacrylate) having a molecular weight of from 5,000 to 5,000,000; poly(vinylpyrrolidone) having a molecular weight of from 10,000 to 360,000; anionic and cationic expandable hydrogels; poly(electrolyte) complexes; poly(vinyl alcohol) having a low acetate residual; a swellable mixture of agar and carboxy-methyl cellulose; a swellable composition comprising methyl cellulose mixed with a sparingly cross-linked agar; a water-swellable copolymer reduced by a dispersion of finely divided copolymer of maleic anhydride with styrene, ethylene, propylene, or isobutylene; water swellable polymer of N-vinyl lactams; and the like.

Other hydrogel or gelable fluid absorbing or imbibing and retaining polymers useful for forming hydrophilic, expandable push member 18 include pectin having a molecular weight ranging from 30,000 to 300,000; polysaccharides such as agar, acacia, karaya, tragacanth, algins and guar; Carbopol ® acidic carboxy polymer and its salt derivatives; polyacrylamides; water-swellable indene maleic anhydride polymers; Good-rite ® polyacrylic acid having a molecular weight of 80,000 to 200,000; Polyox ® polyethylene oxide polymers having a molecular weight of 10,000 to 5,000,000; starch graft copolymers; Aqua-Keep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000, and the like. In a preferred embodiment, the expandable member is formed from polymer and polymeric compositions that are thermoformable, and embrace a different molecular structure than the structure comprising osmopolymer 17. Representative polymers possessing hydrophilic properties are known in U.S. Pat. Nos. 3,865,108; 4,002,173; 4,207,893, 4,327,725, and in *Handbook of Common Polymers*, by Scott and Roff, published by Cleveland Rubber Company, Cleveland, OH.

Agent carrier means 17, used for forming with a beneficial agent a dispensable formulation, is a hydrophilic polymer that exhibits the ability to absorb or to imbibe and retain fluid and form a viscous solution or a semipaste like carrier. The carrier containing the imbibed fluid and the beneficial agent is dispensed through passageway 13 from device 10. The fluids imbibed into compartment 14 are aqueous and aqueous-biological fluids. In a presently preferred embodiment carrier means 17 is a noncrosslinked hydrogel and it is preferably a different hydrogel than expandable member 18. Generally, the hydrogel of carrier means 17 will have a viscosity of about 100 centipoise at a 5% concentration to a solution viscosity of 1000 centipoise at a 5% concentration measured at 25° C. For the purpose of this invention, the viscosity of expandable means 18 is greater than the viscosity of carrier means 17, usually by at least 4,000 centipoises. The solution viscosity of a polymer can be measured using a Brookfield viscometer. Methods for measuring viscosity are disclosed in *Pharmaceutical Sciences*, by Remington, 14th Ed., pp 361 to 371, 1970, published by Mack Publishing Co., Easton, PA. Methods for measuring molecular weight are disclosed in *Encyclopedia of Chemistry*, by Clark, 2nd Ed., pp 663 to 667, 1966, published by Van Nostrand Reinhold Co., NY; and in *Handbook of Common Polymers*, by Scott, Sect. 52, pp 487 to 493, 1971, published by Chemical Rubber Co., Cleveland, OH.

The osmotically effective compound that can be blended with the beneficial agent are the osmotically effective solute that are soluble in fluid imbibed into the compartment, and exhibit an osmotic pressure gradient across the semipermeable wall against an exterior fluid. Osmotically effective compounds are known in the dispensing art also as osmagents. Osmotically effective osmagents useful for the present purpose include magnesium sulfate, magnesium chloride, sodium chloride, lithium chloride, potassium sulfate, sodium sulfate, mannitol, urea, sorbitol, inositol, succrose, glucose, and the like. The osmotic pressure in atmospheres, atm, of the osmagents suitable for the invention will be greater than zero atm, generally from eight atm up to 500 atm, or higher. Generally the compartment will contain optionally from 0.1% by weight to 40% by weight of osmagent. The osmagent form an aqueous solution containing a beneficial agent dissolved therein, or when the agent is insoluble in aqueous and biological fluid a suspension is formed in situ. Those versed in the art can easily select an osmagent and determine its osmotic pressure with any commercial available osmometer. A detailed description of osmagents is presented in U.S. Pat. No. 4,008,716.

The weight increasing means, or density means used to form the dense member 19, or for blending with expandable polymer 18, or for blending with the beneficial agent, which density increasing member is used for initially retaining device 10 in the rumen-reticular sac of a ruminant. The dense member designed as densifier 19, or when homogeneously or heterogeneously blended with expandable polymer 18 is used initially for retaining dispensing device 10 in the rumen-reticular sac of a ruminant In the embodiment comprising the dense member blended with the beneficial agent, dispensing device 10 remains in the rumen during the dispensing period and then it passes into the alimentary tract and is eliminated therefrom. Generally dense member 19 will have a density of from greater than about 1 to about 8 or higher, and when formulated with expandable polymer 18, or with beneficial agent 15, the amount of weight means mixed therewith will be an amount sufficient to impart an initial density to the expandable hydrogel, or to the beneficial agent formulation of from 1 to 8, with the density in a presently preferred embodiment exhibiting a specific gravity of from 2.0 to 7.6. For ruminant cattle and sheep, it is presently preferred the densifier, or the combination, initially exhibit a density such that there is a resulting system density of about 3. Materials that have a density of from 1 to 8 include iron, iron shot, iron shot coated with iron oxide, iron shot magnesium alloy, steel, stainless steel, copper oxide, a mixture of cobalt oxide and iron powder, a mixture of iron and copper oxide, and the like. The weight means can be in powder, granule, pellet and like form for forming the densifier or for blending with the beneficial agent or with the expandable hydrogel. The weight means can be blended with the hydrogel during polymerization, by blending solvent casting and evaporating, by compressing a blend and the like. The weight increasing means can be formulated with the beneficial agent by blending in a commercial v-blender and then compressing in a tableting machine. The amount of weight blended with the expandable hydrogel, or with the beneficial agent is about 0.5 to 50 weight percent, or an amount sufficient to produce the desired density. Density, specific gravity and specific volume determinations are easily performed by procedures known in the art as disclosed in Remington's Pharmaceutical Sciences, Vol. 14, pp 95 to 100, edited by Osol, 1970, by Mack Publishing Company, Easton, OH.

The term "beneficial agent" as used herein includes medicines or drugs, nutrients, vitamines, anthelminthic, biocide, parasiticide, food supplements, and other agent that benefit a ruminant animal. The beneficial agent can be insoluble to very soluble in the aqueous carrier means formed in situ in the delivery system. The amount of agent present in a delivery system can be from 10 ng to 40 g or more. The delivery system can house various amounts of the beneficial agent, for example, 75 ng, 1 mg, 5 mg, 100 mg, 250 mg, 750 mg, 1.5 mg. 2 g, 5 g, 10 g, 15 g, and the like. A single delivery system can be administered to a ruminant, or more than one delivery system can be administered to a ruminant during a therapeutic program.

Representative of beneficial agent that can be dispensed using the delivery system of this invention include anthelminthics such as mebendazole, levamisole, albendazole, cambendazole, fenbendazole, parbendazole, oxfendazole, oxybendazole, thiabendazole, tichlorfon, praziquantel, oxantel and pyrantel, and the like. Antiparasitic agent such as avermectin and ivermectin, as disclosed in U.S. Pat. Nos. 4,199,569 and 4,389,397, and in Science, Vol 221, pp 823-828, 1983, wherein said ivermectin antiparasitic drug is disclosed as useful for aiding in controlling commonly occurring infestations in animals, such as roundworms, lungworms, and the like, and said ivermectin also being useful for management of insect infestations such as grub, lice, mange mite, and the like; avermectin and milbemycin phosphate; antimicrobial agents such as chlortetracycline, oxytetracycline, tetracycline, streptomycin, dihydrostreptomycin, bacitracins, erythromycin, ampicillins, penicillins, cephalosporins, and the like; sulfa drugs such as sulfamethazine, sulfathiazole, and the like; growth stimulants such as Monesin ® sodium, efrotomycin, and Elfazepam ®; defleaing agents such as dexamethazone and flumethazone; rumen fermentation manipulators and ionophores such as lasalocid, salinomycin, virginamycin and ronnel; minerals and mineral salts including copper oxide, cobalt sulphate, sodium selenite, zinc oxide, manganese sulphate, zinc sulphate, and the like; anti-bloat agents such as organopoly siloxanes; hormone growth supplements such as stilbestrol; vitamins such as thiamine hydrochloride, antienteritis agents such as furazolidone; nutritional supplements as as lysine monohydrochloride, methionine, magnesium carbonate, soluble salts of magnesium, copper and selenium, and the like.

The wall forming compositions can be applied to form the device or as the exterior surface of the capsule in laminar arrangement by molding, air spraying, dipping, casting, or brushing, with a semipermeable wall forming composition. Other and presently preferred techniques that can be used for applying the wall are the air suspension procedure and the pan coating procedure. The air procedure consists in suspending and tumbling the compressed arrangement of the device forming components in a current of air and a semipermeable wall forming composition until the wall surrounds and coats the components or surrounds and coats the capsule member. The procedure can be repeated with a different semipermeable wall forming composition to form a semipermeable laminated wall. The air suspension procedure is described in U.S. Pat. No. 2,799,241; J. Am. Pharm. Assoc., Vol. 48, pp 451–459, 1979; and ibid., Vol. 49, pp 82–84, 1960. Other standard manufacturing procedures are described in Modern Plastics Encyclopedia, Vol 46, pp 62–70, 1969; and in Pharmaceutical Sciences, by Remington, 14th Ed., pp 1626–1678, 1970, published by Mack Publishing Company, Easton, PA.

Exemplary solvents suitable for manufacturing the semipermeable wall include inert inorganic and organic solvents that do not adversely harm the materials, the capsule wall, the beneficial agent, and fluid responsive composition, the expandable member, the dense member, and the final dispenser. The solvents broadly include members selected from the group consisting of aqueous solvents, alcohols, ketones, esters, ethers, aliphatic hydrocarbons, halogenated solvents, cyclo-aliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naptha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol, and the like.

The expression "passageway" or "orifice" as used herein comprises means and methods in the wall or in a laminated wall suitable for releasing a beneficial agent formulation from the dispenser. The passageway can be formed by mechanical or laser drilling, or by eroding an erodible element in the wall, such as a gelatin plug. The passageway can be drilled through the wall only, or through the wall-capsule, laminated wall. In these embodiments when the passageway is drilled only through the wall, the passageway in the capsule wall is formed in the environment of use by bursting, eroding or dissolving a passageway in the capsule wall. The passageway can be a porous polymer composition having at least one pore, or a microporous polymer composition having at least one micropore or more than one micropores that serve as more than one passageway suitably made a part of the wall of the delivery system. The passageway can be positioned in a preselected loci of the wall by visual inspection, by optical density scanning as the device travels through a laser machine, by orienting and following the device through the manufacturing steps, by photo detection and responding to the reflected wave length emanating from a device, by magnetic orientation, and like standard manufacturing procedures. A detailed description of some orifice and the preferred maximum and minimum dimensions for an orifice are disclosed in U.S. Pat. Nos. 3,845,770 and 3,916,899.

DESCRIPTION OF EXAMPLES OF THE INVENTION

The following examples are merely illustrative of the present invention and they should not be construed as limiting the scope of the invention in any way, as these examples and other equivalents thereof will become more apparent to those skilled in the art in the light of the present disclosure, the drawings and the accompanying claims.

EXAMPLE 1

A veterinary dispensing device for the controlled delivery of ivermectin is made as follows: first, an expandable driving member comprising 1.2 g of sodium chloride and 4.6 g of the sodium salt of poly(acrylic acid) available as Carbopol ® 934-P are compressed into a solid mass shaped like a tablet. The tablet is formed using a Manesty press, a 18 mm tableting tool and 3½ tons of compression force to yield the tablet. The tablet has a final shape that corresponds to the internal shape of the opening of a capsule. Next, the tablet member is inserted into the opened end of the capsule until contact is made with the bottom of the capsule. Then the capsule is charged with a layer of beneficial agent formulation. The formulation comprises 4 g of ivermectin homogeneously blended with 1.6 g of poly(vinyl pyrrolidone), 1.2 g of magnesium stearate, and 0.5 g of sodium chloride. The ingredients are thoroughly blended with a v-blender and pressed in a Manesty press under a pressure head of 1½ tons to produce a tablet shaped layer that is inserted into the capsule in contacting arrangement with the expandable hydrogel layer. Then, a dense stainless steel element having an internal bore and a shape that matches the inside of the capsule is placed in the capsule in contacting arrangement with the beneficial agent formulation. Next, the capsule is coated in a pan coater with a rate controlling wall comprising 1.8 g of 91% cellulose acetate butyrate and 9% polyethylene glycol 400. The wall is coated from a 5% wt/wt solution in methylene chloride methanol 90:10 v/v solvent system. The wall coated delivery systems then are dried at 30° C. for 24 hours. Next, the device is visually oriented and a 30 mil exit passageway is drilled through the semipermeable wall and the gelatin capsule using a high speed mechanical drill for communicating the passageway with the bore of the densifier and, hence, the internal compartment of the device. The passageway establishes communication with the beneficial agent formulation for delivering it from the delivery device over time.

EXAMPLE 2

A dispensing device is made according to the procedure set forth in Example 1, with the conditions as set forth, except that in this example the densifier was replaced by the addition of a dense member to the expandable polymer. The expandable-swellable composition comprises 70% by weight of poly(ethylene oxide) having a molecular weight of 3,000,000; 10% by weight of sodium chloride, and 20% by weight of a 50:50 mixture of cobalt and iron shot.

EXAMPLE 3

A dispenser system is prepared as follows: first, the body section of a capsule is positioned with its mouth in an upright position, and a layer of an expandable-swellable density composition is charged into the hemispherical end of the capsule. The layer's shape matches the internal shape of the capsule. The composition comprises 5% by eight of sodium chloride, 70% by weight of poly(ethylene oxide) having a molecular weight of 200,000 and 25% by weight of stainless steel tiny particles. The expandable-swellable density composition forming ingredients are blended in a commercial blender with heat for 20 minutes to yield a homogeneous composition. The heated composition is charged into the capsule forming a layer that occupies about ⅓ of the capsule. Next, a beneficial agent formulation is added to the capsule in overlay position with the expandable density composition. The beneficial agent formulation is an osmotically active aqueous imbibing formulation comprising 70% by weight of levamisole, 10% by weight of sorbitol, 15% by weight of poly(vinyl pyrrolidone), and 5% by weight of calcium stearate.

Then a solution of cellulose acetate, 15 weight percent, with an acetyl content of 39.8%, is prepared in a methylene chloride methanol solvent system and the capsule coated with a semipermeable wall. The wall is applied by dipping it into the coating solution for 15 times, first for a 5 second dip, then for two 10 second dips, then for a 30 second dip and then for 1 minute per dip, with an intervening 5 minute drying period. Following the dipping the delivery dispenser is dried at room temperature, 72° F., about 22° C., for 5 days. The procedure applies about a 2 mm thick semipermeable wall. A passageway positioned by photo detection is laser drilled through the semipermeable wall connecting the exterior of the dispenser with the beneficial agent formulation for releasing it in a fluid environment at a controlled rate over time.

EXAMPLE 4

A dispensing system for delivering beneficial agent to warm-blooded ruminants is prepared as follows: first, a mold having a shape and configuration corresponding to the internal diameter and the hemispherical closed end of a capsule, is filled with an expandable density forming composition comprising 30 parts of ethyleneglycol monomethacrylate containing 0.12 parts of ethylenegTycol dimethacrylate, 10 parts of a 0.13% aqueous solution of sodium disulfate in aqueous ethanol, and 30 parts of iron powder and magnesium. The composition polymerizes at 30° C., and after 20 minutes following equilibrium to room temperature, the solid layer is removed from the mold. The solid expandable layer then is inserted through the mouth of the capsule into the hemispherical area of the capsule. Next, the capsule is filled with a beneficial agent formulation consisting essentially of 50% morantel tartrate, 20% polyethylene glycol, 6% sodium hexamethaphosphate and 24% sodium chloride in laminar position with the expandable dense member. Next, the filled capsule is coated with a surrounding wall comprising cellulose acetate containing 10% polyethylene glycol 400. The semipermeable wall is applied in a pan type Hi-coater. The solvent used for forming the wall consists essentially of methylene chloride and methanol 95 parts by weight to 5 parts by weight. A 12 mil (0.30 mm) thick wall of cellulose acetate butyrate is applied to the exterior surface of the capsule. Finally, a passageway is laser drilled through the semipermeable wall and the capsule wall communicating with the beneficial agent containing composition for its delivery to the environment of use.

EXAMPLE 5

The procedure of Example 1, is repeated with the exception that the beneficial agent is replaced by anthelmintic pyrantel tartrate, pyrantel pamoate or pyrantel embonate; anthelminthic tetramisole hydrochloride; anthelminthic diethylcarbamazine hydrochloride or diethylcarbamazine citrate; anthelminthic oxantel hydrochloride, oxantel embonate or oxantel pamoate; antibacterial avoparcin; antibloat poloxalene; and antiparasitic avermectin A$1a$, avermectin A$2a$, avermectin B$1a$ or avermectin B$2a$.

EXAMPLE 6

A delivery device is made according to the procedure set forth in Example 1, with the conditions and materials as set forth, except that in this example a varying rate controlling wall thickness comprising cellulose acetate butyrate and polyethylene glycol 400 is applied to the device. The thickness of the rate controlling wall varies from 30 mil (0.76 mm) at the end distant from the passageway in a uniform taper to 15 mil (0.38 mm) adjacent to the density member.

EXAMPLE 7

A delivery device is prepared by following the procedures set forth above. The delivery device comprises a first compressed composition comprising 36 g of poly(ethylene oxide) having a molecular weight of 500,000, 30 g of iron powder and 5 g of sodium chloride, pressed against a second compressed composition comprising 1.7 g of parbendazole, 38.5 g of polyvinyl pyrrolidone, and 9.7 g of sodium chloride. The laminated compressed layers are surrounded with a semipermeable wall that comprises 50% cellulose acetate butyrate, 45% poly(sulfone) and 5% citroflex citric acid ester selected from the group consisting of acetyl tributyl citrate and acetyl tri-2-ethyl-hexyl citrate. The device has a passageway through the semipermeable wall connecting the beneficial drug formulation with the exterior of the device.

EXAMPLE 8

A delivery system is made according to the procedure as set forth in Example 7, with all conditions as described except that the semipermeable wall comprises 80% cellulose acetate butyrate and 20% poly(sulfone), or 20% cellulose acetate butyrate and 80% poly(sulfone).

EXAMPLE 9

A veterinary delivery device is prepared according to Example 7, with the conditions as described except that the delivery device of this example comprises a high density poly(ethylene) tubular wall surrounding an internal lumen, closed at one end with a cellulose acetate film having an acetyl content of 39.5% for imbibing fluid therethrough by the contacting expandable hydrogel, and closed at its other ends by a microporous poly(tetrafluoroethylene) film for dispensing contacting beneficial agent formulation from the dispensing device.

An embodiment of the invention pertains to (1) a method of increasing the deliverability of a beneficial agent by formulating a deliverable composition containing a beneficial agent and (2) making the delivery system of the invention for increasing the deliverability of the beneficial agent. An embodiment of the invention pertains also to a method for administering a beneficial agent at a controlled rate to the rumen of the ruminant, which method comprises the steps of: (A) admitting into the rumen a dispensing device comprising (1) an outer wall formed in at least a part of a semipermeable polymeric composition permeable to the passage of fluid and substantially impermeable to the passage of beneficial agent, the wall surrounding (2) an internal lumen containing a layer of beneficial agent formulation comprising a dosage unit amount of agent for performing a therapeutic program in an aqueous or biological fluid sensitive pharmaceutically acceptable carrier that imbibes fluid at an animal body temperature and is correspondingly a means for transporting the agent from the dispenser; (3) a layer of an expandable hydrogel in the lumen, said layer an expandable hydrogel containing a density producing member for maintaining the dispenser in the rumen over a prolonged period of time; or, a density member in the lumen for maintaining the dispenser in the rumen over a prolonged period of time; and (5) an orifice through the wall communicating with the fluid sensitive agent formulation; (B) imbibing fluid through the semipermeable wall at a rate determined by the permeability of the semipermeable wall and the osmotic pressure gradient across the semipermeable wall causing the hydrogel to expand and swell; (C) imbibing fluid into the beneficial agent formulation to form a dispensable flowable aqueous-like solution, or an aqueous-like suspension formulation in situ at the temperature use; and (D) delivering the beneficial agent formulation from the compartment by the expandable hydrogel continually expanding against the dispensable formulation causing the formulation to be dispensed in a therapeutically effective amount through the orifice at a controlled rate to the rumen over a prolonged period of time.

Inasmuch as the foregoing specification comprises preferred embodiments of the invention, it is understood that variations and modifications may be made herein in accordance with the inventive principles disclosed, without departing from the scope of the invention.

I claim:

1. A dispensing device for delivering a beneficial agent formulation to an aqueous environment of use, the dispensing device comprising:
   (a) wall means for surrounding and forming an internal compartment, said wall means comprising in at least a part a semipermeable composition permeable to the passage of aqueous fluid present in the environment of use;
   (b) a beneficial agent formulation in the compartment, which beneficial agent formulation exhibits an osmotic pressure gradient across the semipermeable wall against an aqueous fluid present in the environment of use and forms with the aqueous fluid that enters the compartment through the wall a dispensable aqueous beneficial agent formulation;

(c) means in the compartment for absorbing aqueous fluid from the environment of use for occupying an increasing amount of space in the compartment;
(d) means in the compartment for increasing the weight of the dispensing device, said means having a density from 1 to 8 and in contact with at least one of said beneficial agent formulation or said means for absorbing aqueous fluid; and,
(e) means in the wall connecting the exterior of the dispensing device with the compartment for delivering the beneficial agent aqueous formulation to the environment of use.

2. The dispensing device for delivering the beneficial agent formulation to the environment of use according to claim 1, wherein the means in the compartment for increasing the weight of the dispensing device comprises a unit body shaped and sized for occupying a selected area of the internal compartment.

3. The dispensing device for delivering the beneficial agent formulation to the environment of use according to claim 1, wherein the means in the wall connecting the exterior of the device with the compartment comprises at least one passageway in the wall.

4. The dispensing device for delivering the beneficial agent formulation to the environment of use according to claim 1, wherein the means in the wall connecting the exterior of the device with the compartment comprises at least two passageways in the wall.

5. The dispensing device for delivering the beneficial agent formulation to the environment of use according to claim 1, wherein the beneficial agent formulation comprises a member selected from the group consisting of an osmagent and an osmopolymer.

6. The dispensing device for delivering the beneficial agent formulation to the environment of use according to claim 1, wherein the means for absorbing fluid is an expandable hydrogel.

7. The dispensing device for delivering the beneficial agent formulation to the environment of use according to claim 1, wherein the beneficial agent formulation comprises a member selected from the group consisting of mebendazole, levamisole, albendazole, cambendazole, fenbendazole, parbendazole, oxfendazole, thiabendazole, tichlorfan, praziquantel, morantel, pyrantel, avermectin, ivermectin, oxantel, piperazine, diethylcarbamazine, tetramisole, polaxalene, selenium, and zearalanol.

8. A dispensing device for delivering a beneficial agent formulation to an aqueous-fluid environment of use, wherein the dispensing device comprises:
(a) wall means for surrounding and forming an internal compartment, said wall comprising in at least a part a composition pervious to the passage of an aqueous fluid present in the environment of use;
(b) means in the compartment for absorbing and imbibing aqueous fluid into the compartment for expanding and occupying an increasing volume of the compartment;
(c) a beneficial agent formulation in the compartment, said beneficial agent formulation imbibing aqueous fluid into the compartment for forming with the beneficial agent a dispensable aqueous-like formulation;
(d) means in the compartment for increasing the weight of the dispensing device, said means having a density from 1 to 8 and comprising a solid unit body and positioned between the beneficial agent formulation and the means for expanding in the compartment, and wherein upon the means for expanding absorbs and imbibes aqueous fluid said means expands and pushes said means for increasing the weight of the dispensing device against said beneficial agent aqueous formulation, whereby said beneficial agent aqueous formulation is pushed into;
(e) passageway means in the dispensing device for delivering the beneficial agent aqueous formulation to the environment of use.

* * * * *